US00PP15246P2

(12) United States Plant Patent
Trees

(10) Patent No.: US PP15,246 P2
(45) Date of Patent: Oct. 19, 2004

(54) ***LANTANA* PLANT NAMED 'BALANDROGLO'**

(50) Latin Name: *Lantana camara*
Varietal Denomination: Balandroglo

(75) Inventor: Scott C. Trees, Shell Beach, CA (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 10/741,700

(22) Filed: Dec. 19, 2003

(51) Int. Cl.[7] ..... A01H 5/00
(52) U.S. Cl. ..... Plt./227
(58) Field of Search ..... Plt./227

*Primary Examiner*—Kent Bell
(74) *Attorney, Agent, or Firm*—Wood, Phillips, Katz, Clark & Mortimer

(57) ABSTRACT

A new and distinct *Lantana* plant named 'Balandroglo' characterized by its flowers that change from yellow-orange when first open to bright rose at full maturity, dark green-colored foliage, and an upright and mounded growth habit.

1 Drawing Sheet

Latin name of genus and species of plant claimed: *Lantana camara.*
Variety denomination: 'Balandroglo'.

BACKGROUND OF THE INVENTION

The present invention relates to a new and distinct cultivar of *Lantana* plant botanically known as *Lantana camara* and hereinafter referred to by the cultivar name 'Balandroglo'.

The new cultivar was developed by the inventor in a controlled breeding program during January 2000 at Arroyo Grande, Calif. The objective of the breeding program was the development of *Lantana* cultivars with a well-branched, compact habit, continuous flowering and dark green foliage.

The new cultivar was the product of the open pollination of the commercially available *Lantana* cultivar 'Simon White' (not patented), characterized by its white-colored flowers, medium green-colored foliage and upright growth habit. 'Balandroglo' was selected in February 2001 as a single flowering plant within the progeny of the above stated open-pollination and was initially designated '194-1'.

Asexual reproduction of the new cultivar by terminal stem cuttings taken since May 2000 at Arroyo Grande, Calif. and West Chicago, Ill. has demonstrated that the new cultivar reproduces true to type, with all the characteristics, as herein described, firmly fixed and retained through successive generations of such asexual propagation.

SUMMARY OF THE INVENTION

The new cultivar has not been observed under all possible environmental conditions to date. Accordingly, it is possible that the phenotype may vary somewhat with variations in the environment, such as temperature, light intensity, and day length without, however, any variation in genotype.

It was repeatedly found that the cultivar of the present invention:

1. Exhibits flowers that change from yellow-orange when first open to bright rose at full maturity,
2. Forms dark green-colored foliage, and
3. Exhibits an upright and mounded growth habit.

Plants of the new cultivar differ from plants of the female parent primarily in flower color and growth habit.

Of the many *Lantana* cultivars known to the inventor, the most similar to 'Balandroglo' is the commercially available *Lantana* cultivar 'Anthens Select Rose', not patented. However, in side-by-side comparisons, plants of the new cultivar differ from plants of the cultivar 'Anthens Select Rose' in the following characteristics:

1. Plants of the new cultivar are shorter than plants of the cultivar Athens Select Rose, and
2. Plants of the new cultivar have smaller leaves than plants of the cultivar Athens Select Rose.

BRIEF DESCRIPTION OF THE PHOTOGRAPHS

The accompanying photographs show as nearly true as it is reasonably possible to make the same in color illustrations of this type, typical flower and foliage characteristics of the new cultivar. Colors in the photographs differ slightly from the color values cited in the detailed description, which accurately describes the colors of 'Balandroglo'. The plants were grown for 10 weeks in a greenhouse at West Chicago, Ill.

DETAILED BOTANICAL DESCRIPTION

Figure 1:
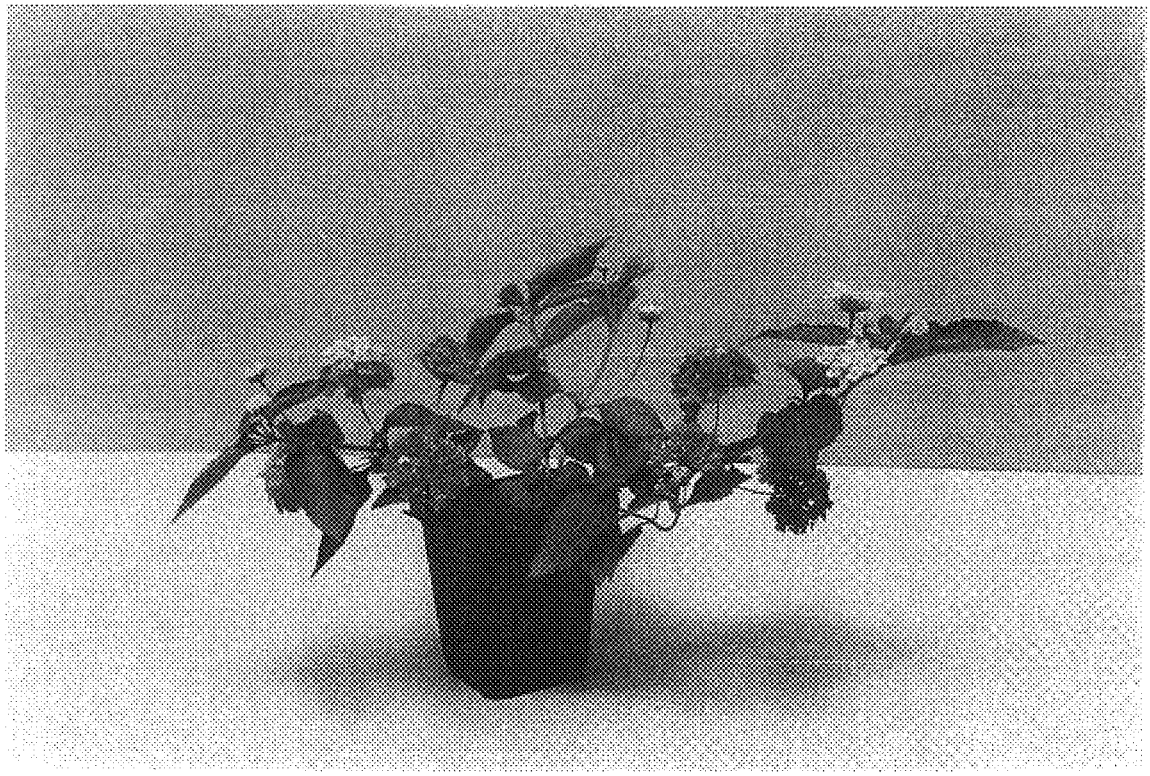
FIG. 1 illustrates a side view of the overall growth and flowering habit of 'Balandroglo'.
Figure 2:
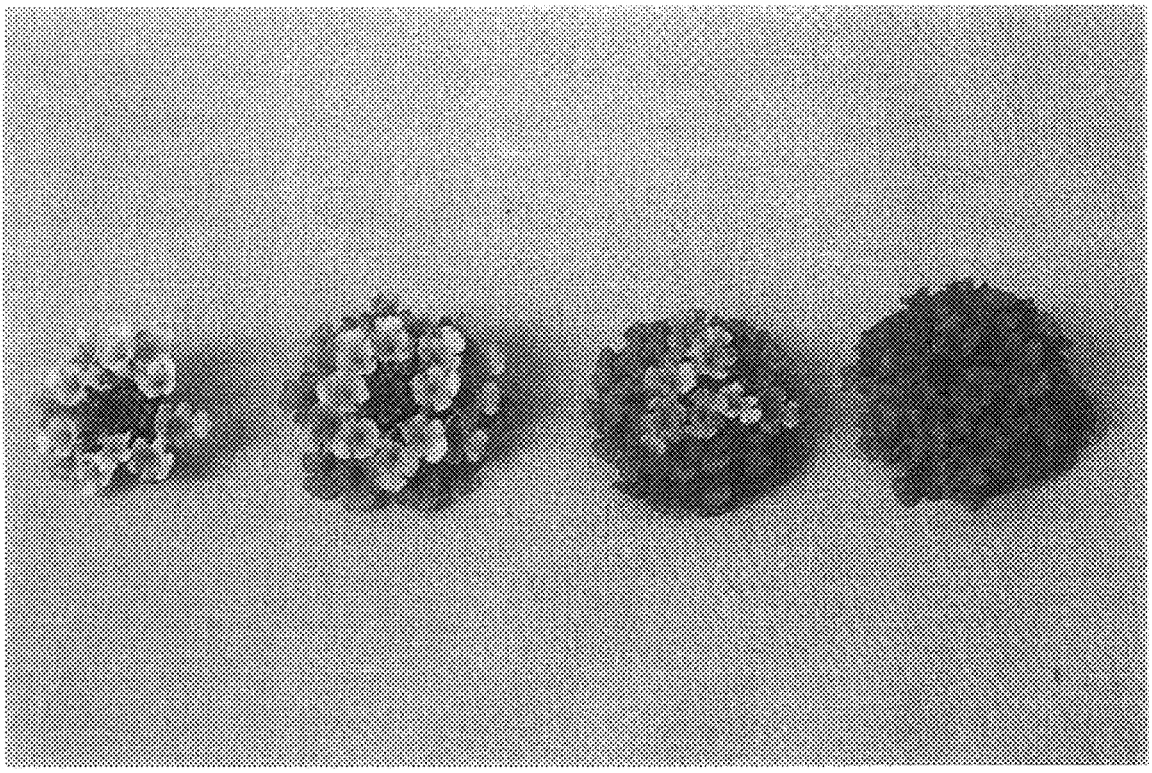
FIG. 2 illustrates a close-up view of four inflorescences of 'Balandroglo' showing how the flowers change from yellow-orange when first open to bright rose at full maturity.

The chart used in the identification of colors described herein is The R.H.S. Colour Chart of The Royal Horticultural Society, London, England, 1995 edition, except where general color terms of ordinary significance are used. The color values were determined on Jul. 22, 2003. The readings were taken between 9:00 and 11:00 a.m. under natural day light conditions. The plants were produced from terminal stem cuttings taken from stock plants and were grown in a double polycarbonate-covered greenhouse under conditions comparable to those used in commercial practice. The plants were grown in 10 cm pots for 10 weeks while utilizing a soilless growth medium in a greenhouse at West Chicago, Ill. Greenhouse temperatures were maintained at approximately 75°–85° F. (24°–29° C.) during the day and approximately 62°–68° F. (17°–20° C.) during the night. Greenhouse light levels were maintained at 4,000–10,000 footcandles during the day.

Botanical classification: *Lantana camara* cultivar 'Balandroglo'.

Parentage: Open pollination of the *Lantana* cultivar Simon White, not patented.

Propagation:

*Type cutting.*—Terminal stem cutting.

*Time to initiate roots.*—Approximately 7 to 11 days.

*Time to develop roots.*—Approximately 4 weeks.

*Root description.*—Fine, fibrous.

*Rooting habit.*—Freely branching.

Plant description:

*Habit of growth.*—Vigorous. Forms lateral branches at every node. Pinching enhances basal branching. A mature plant, 10 weeks after the planting of a rooted cutting, measures approximately 15.3 cm in height from soil level to top of plant plane and approximately 47.6 cm in diameter (area of spread) with 3.3 main branches.

*Form.*—Upright, mounded and spreading.

*Branch.*—Shape: Quadrilateral. Strength: Strong. Length: Approximately 23.6 cm. Diameter: Approximately 2.9 mm. Texture: Moderately pubescent with short stiff hairs. Color of young supple branch: 144A. Color of mature woody branch: N199A. Internode length at middle of stem is approximately 4.1 cm.

*Foliage.*—Type: Simple. Arrangement: Opposite. Orientation to stem: 90° angle. Fragrance: Faint, spicy. Shape: Ovate. Margin: Crenate. Apex: Acute. Base: Cuneate. Texture of upper surface: Moderately pubescent. Texture of lower surface: Densely covered with short, stiff hairs. Leaf length: Approximately 7.9 cm. Leaf width: Approximately 4.3 cm. Venation pattern: Pinnate. Color of upper surface of mature foliage: Closest to 147A with veins of 145C. Color of lower surface of mature foliage: 147B with veins of 145C. Petiole length: Approximately 1.2 cm. Petiole diameter: Approximately 2 mm. Petiole texture: Upper surface: Densely covered with short, stiff hairs. Lower surface: Dense stiff hairs with moderate amount of glandular pubescence. Gland color: Colorless, translucent. Petiole color of both surfaces: 144A.

Flowering description:

*Flowering habit.*—Freely flowering.

*Natural flowering season.*—Year round in greenhouse environment and spring through autumn in outdoor garden.

Inflorescence description:

*Type.*—Corymb.

*Shape.*—Spherical.

*Number per plant.*—Approximately 5.

*Size.*—Depth (height): Approximately 2.2 cm. Diameter: Approximately 4.2 cm. Number of flowers per inflorescence: Approximately 37 fully opened flowers at any one time. Each flower is subtended by a single bract.

*Bract.*—Shape: Lanceolate. Length: Approximately 4 mm. Width: Approximately 1 mm. Apex: Acute. Margin: Entire. Texture: Upper surface: Moderate pubescent with a mixture of short non-glandular hairs and short glandular hairs. Gland color: Colorless and translucent. Lower surface: Densely pubescent. Color of both surfaces: 144B.

*Peduncle.*—Shape: Quadrilateral. Length: Approximately 6.2 cm. Diameter: Approximately 1 mm. Aspect: At acute angle to branch. Texture: Pubescent with short stiff hairs. Color: 144B.

Flower description:

*Shape.*—Salverform.

*Fragrance.*—Light, sweet.

*Aspect.*—Concave.

*Lastingness of bloom.*—Approximately 8 days from first color of outer buds to dropping of last floret.

*Bud.*—Shape: Roughly spherical. Length: Approximately 3 mm. Width: Approximately 3 mm. Color: 29C.

*Corolla size.*—Diameter: Approximately 1.1 cm.

*Petals.*—Five, non-imbricate, non-symetrical, fused at base forming corolla tube. Shape: Obovate. Margin: Entire, ruffled. Texture of upper and lower surfaces: Glabrous. Length from throat: Approximately 5 mm. Petal color when first open: Upper surface: 4B with 13A around throat opening. Lower surface: 4D. Petal color when fully open: Upper surface: N74C with 33A around throat opening. Lower surface: 75C. Petal color when fully mature: Upper surface: N74B. Lower surface: 73D.

*Upper petal.*—Apex: Cuspidate. Width: Approximately 6 mm.

*Lateral petals.*—Apex: Obtuse. Width: Approximately 5 mm.

*Lower petal.*—Apex: Cuspidate. Width: Approximately 6 mm.

*Corolla tube.*—Length: Approximately 1.5 cm. Diameter at tube opening: Approximately 1.4 mm. Diameter at base: Approximately 0.8 mm. Texture of outer surface of tube: Densely covered with short hairs. Texture of inner surface: Glabrous except for hairs around opening. Color of both inner and outer surface: First open: 31C. Fully open: 35C. Mature: 72D.

*Calyx.*—Shape: Tubular. Length: Approximately 2 mm. Diameter: Approximately 1.5 mm. Texture: Densely pubescent. Color: 145C.

*Reproductive organs.*—Stamens: Four per flower, adnate to the corolla tube. Filament length of free portion: 1 mm. Filament color: 155A. Anther shape: 2 lobed, lanceolate. Anther length: 1 mm. Anther color: 162A. Amount of pollen: None observed. Pistil quantity: One per flower. Pistil length: 4.5 mm. Stigma shape: Oval. Stigma length: 0.5 mm. Stigma color: 154D, translucent. Style length: Approximately 3 mm. Style color: 145D. Ovary length: 1 mm. Ovary color: 151D.

Seed and fruit production: Neither seed nor fruit production has been observed.

Disease and pest resistance: Resistance to pathogens or pests common to *Lantana* has not been observed.

Hardiness zone: 'Balandroglo' is hardy in zones nine (9) and above.

What is claimed is:

1. A new and distinct cultivar of *Lantana camara* plant named 'Balandroglo' substantially, as herein shown and described, which:

1. Exhibits flowers that change from yellow-orange when first open to bright rose at full maturity,
2. Forms dark green colored foliage, and
3. Exhibits an upright and mounded growth habit.

* * * * *